(12) United States Patent
Schenck

(10) Patent No.: US 8,515,553 B2
(45) Date of Patent: Aug. 20, 2013

(54) METHODS AND APPARATUS FOR PREDICTIVELY CONTROLLING THE TEMPERATURE OF A COOLANT DELIVERED TO A TREATMENT DEVICE

(75) Inventor: Alan Schenck, Sunnyvale, CA (US)

(73) Assignee: Thermage, Inc., Hayward, CA (US)

( * ) Notice: Subject to any disclaimer, the term of this patent is extended or adjusted under 35 U.S.C. 154(b) by 1514 days.

(21) Appl. No.: 12/110,384

(22) Filed: Apr. 28, 2008

(65) Prior Publication Data

US 2009/0270954 A1    Oct. 29, 2009

(51) Int. Cl.
*A61N 1/00* (2006.01)

(52) U.S. Cl.
USPC .......................... 607/100; 607/102

(58) Field of Classification Search
USPC .......................... 607/100, 101–104
See application file for complete search history.

(56) References Cited

U.S. PATENT DOCUMENTS

| | | |
|---|---|---|
| 3,948,269 A | 4/1976 | Zimmer |
| 5,195,958 A | 3/1993 | Phillips |
| 5,281,213 A | 1/1994 | Milder et al. |
| 5,348,554 A | 9/1994 | Imran et al. |
| 5,423,811 A | 6/1995 | Imran et al. |
| 5,697,927 A | 12/1997 | Imran et al. |
| 5,735,846 A | 4/1998 | Panescu et al. |
| 5,755,753 A | 5/1998 | Knowlton |
| 5,871,524 A | 2/1999 | Knowlton |
| 5,919,219 A | 7/1999 | Knowlton |
| 5,948,011 A | 9/1999 | Knowlton |
| 6,035,238 A | 3/2000 | Ingle et al. |
| 6,059,780 A | 5/2000 | Gough et al. |
| 6,081,749 A | 6/2000 | Ingle et al. |
| 6,139,569 A | 10/2000 | Ingle et al. |
| 6,216,704 B1 | 4/2001 | Ingle et al. |
| 6,236,891 B1 | 5/2001 | Ingle et al. |

(Continued)

FOREIGN PATENT DOCUMENTS

| | | |
|---|---|---|
| WO | 9916502 | 4/1999 |
| WO | 0053113 | 9/2000 |

(Continued)

OTHER PUBLICATIONS

Schenck, "Apparatus and Methods for Cooling a Treatment Apparatus Configured to Non-Invasively Deliver Electromagnetic Energy to a Patient's Tissue", U.S. Appl. No. 11/952,649, filed Dec. 7, 2007.

(Continued)

*Primary Examiner* — Theodore J Stigell
*Assistant Examiner* — Melissa A Snyder
(74) *Attorney, Agent, or Firm* — Wood, Herron & Evans, LLP

(57) ABSTRACT

Apparatus and methods for predictively controlling the temperature of a coolant delivered to a treatment apparatus configured to non-invasively treat a patient's tissue with doses of electromagnetic energy. The treatment apparatus includes a closed-loop cooling system connected with an energy delivery device used to deliver the electromagnetic energy to the patient's tissue. Coolant is pumped from a reservoir to the energy delivery device in the closed-loop cooling system. The control temperature of the coolant in the reservoir is adjusted based upon the specific room air temperature. This predictive adjustment promotes better control over the coolant temperature at the energy delivery device by lessening the effects of heat gain in transit from the reservoir to the energy delivery device.

13 Claims, 3 Drawing Sheets

(56) References Cited

U.S. PATENT DOCUMENTS

| | | |
|---|---|---|
| 6,241,753 B1 | 6/2001 | Knowlton |
| 6,283,987 B1 | 9/2001 | Laird et al. |
| 6,311,090 B1 | 10/2001 | Knowlton |
| 6,322,584 B2 | 11/2001 | Ingle et al. |
| 6,350,276 B1 | 2/2002 | Knowlton |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,425,912 B1 | 7/2002 | Knowlton |
| 6,430,446 B1 | 8/2002 | Knowlton |
| 6,438,424 B1 | 8/2002 | Knowlton |
| 6,453,202 B1 | 9/2002 | Knowlton |
| 6,461,378 B1 | 10/2002 | Knowlton |
| 6,470,216 B1 | 10/2002 | Knowlton |
| 6,480,746 B1 | 11/2002 | Ingle et al. |
| 6,524,308 B1 | 2/2003 | Muller et al. |
| 6,533,780 B1 | 3/2003 | Laird et al. |
| 6,558,381 B2 | 5/2003 | Ingle et al. |
| 6,572,639 B1 | 6/2003 | Ingle et al. |
| 6,702,808 B1 | 3/2004 | Kreindel |
| 6,719,449 B1 * | 4/2004 | Laugharn et al. ............ 366/127 |
| 6,976,492 B2 | 12/2005 | Ingle et al. |
| 6,997,923 B2 | 2/2006 | Anderson et al. |
| 7,006,874 B2 | 2/2006 | Knowlton et al. |
| 7,022,121 B2 | 4/2006 | Stern et al. |
| 7,090,670 B2 | 8/2006 | Sink |
| 7,115,123 B2 | 10/2006 | Knowlton et al. |
| 7,141,049 B2 | 11/2006 | Stern et al. |
| 7,164,942 B2 | 1/2007 | Avrahami et al. |
| 7,189,230 B2 | 3/2007 | Knowlton |
| D544,955 S | 6/2007 | Carson et al. |
| 7,229,436 B2 | 6/2007 | Stern et al. |
| 7,257,450 B2 | 8/2007 | Auth et al. |
| 7,267,675 B2 | 9/2007 | Stern et al. |
| 7,452,358 B2 | 11/2008 | Stern et al. |
| 7,473,251 B2 | 1/2009 | Knowlton et al. |
| 7,473,252 B2 | 1/2009 | Barry |
| 7,476,242 B2 * | 1/2009 | Matlock ..................... 607/105 |
| 7,481,809 B2 | 1/2009 | Stern et al. |
| 7,494,488 B2 | 2/2009 | Weber |
| 2003/0139790 A1 | 7/2003 | Ingle et al. |
| 2003/0178032 A1 | 9/2003 | Ingle et al. |
| 2003/0216719 A1 | 11/2003 | Debenedictis et al. |
| 2004/0082940 A1 | 4/2004 | Black et al. |
| 2005/0049582 A1 | 3/2005 | DeBenedictis et al. |
| 2005/0171582 A1 | 8/2005 | Matlock |
| 2006/0009750 A1 | 1/2006 | Altshuler et al. |
| 2006/0122668 A1 | 6/2006 | Anderson et al. |
| 2006/0149343 A1 | 7/2006 | Altshuler et al. |
| 2006/0206103 A1 | 9/2006 | Altshuler et al. |
| 2006/0206179 A1 | 9/2006 | Black |

FOREIGN PATENT DOCUMENTS

| | | |
|---|---|---|
| WO | 0100269 | 1/2001 |
| WO | 03053266 | 3/2003 |
| WO | 03065915 | 8/2003 |
| WO | 03065916 | 8/2003 |
| WO | 03086217 | 10/2003 |
| WO | 2004086943 | 10/2004 |
| WO | 2004087253 | 10/2004 |
| WO | 2004088700 | 10/2004 |
| WO | 2004089185 | 10/2004 |
| WO | 2004089186 | 10/2004 |
| WO | 2004089459 | 10/2004 |
| WO | 2004089460 | 10/2004 |
| WO | 2004090939 | 10/2004 |
| WO | 2004105861 | 12/2004 |

OTHER PUBLICATIONS

Schenck, "Leakage-Resistant Tissue Treatment Apparatus and Methods of Using Such Tissue Treatment Apparatus", U.S. Appl. No. 12/142,020, filed Jun. 19, 2008.

Schenck, "Leakage-Resistant Tissue Treatment Apparatus and Methods of Using Same", U.S. Appl. No. 12/142,104, filed Jun. 19, 2008.

USPTO, Office Action issued in related U.S. Appl. No. 12/142,020 dated Nov. 14, 2011.

* cited by examiner

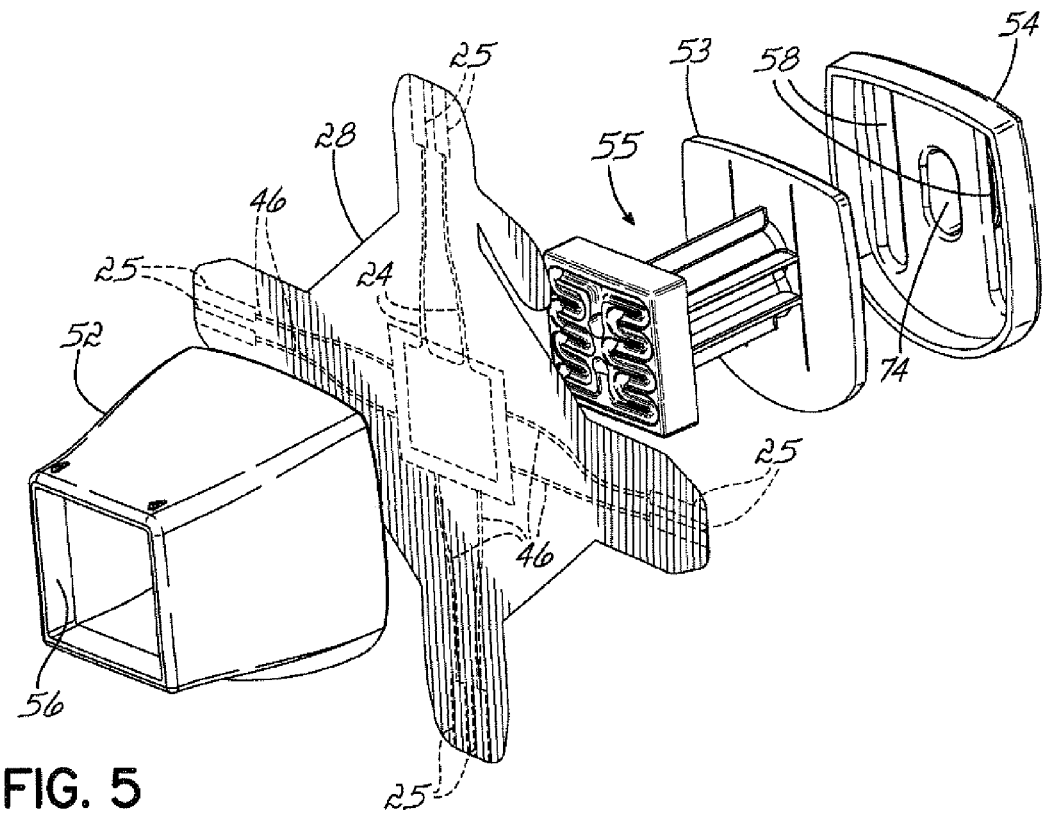
FIG. 5
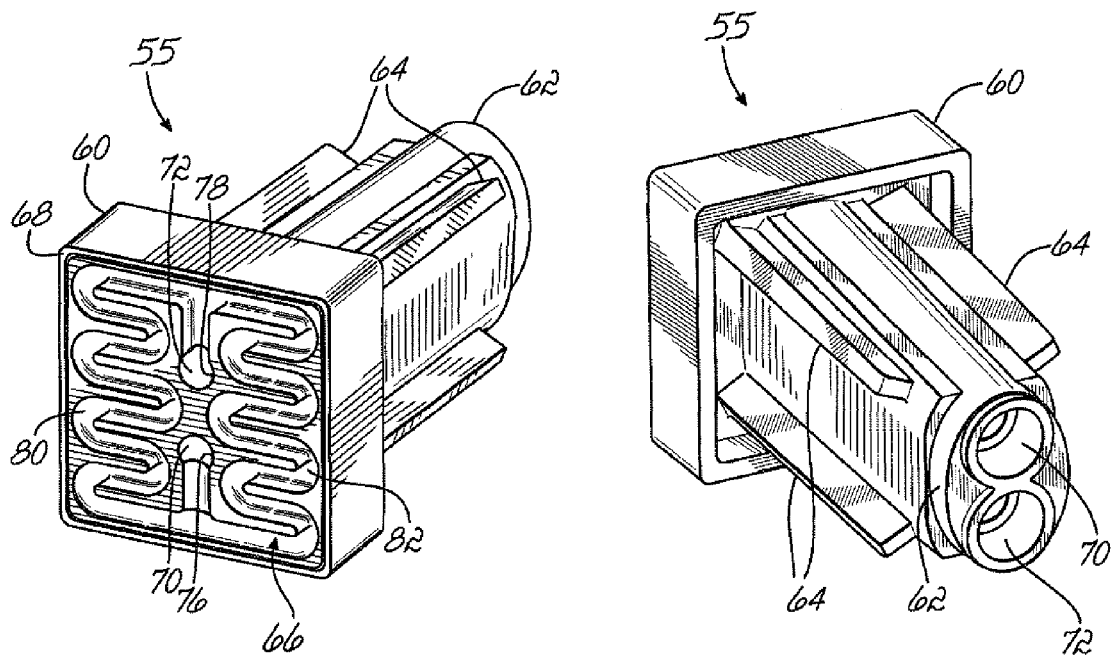
FIG. 6
FIG. 7

METHODS AND APPARATUS FOR PREDICTIVELY CONTROLLING THE TEMPERATURE OF A COOLANT DELIVERED TO A TREATMENT DEVICE

FIELD OF THE INVENTION

The invention generally relates to methods and apparatus for treating tissue with electromagnetic energy and, more particularly, relates to methods and apparatus for predictively controlling the temperature of a coolant delivered to a treatment device and used to cool the tissue during tissue treatment with electromagnetic energy delivered from the treatment device.

BACKGROUND OF THE INVENTION

Certain types of energy delivery devices are capable of non-ablatively and non-invasively treating a patient's tissue with electromagnetic energy. These energy delivery devices, which emit electromagnetic energy in different regions of the electromagnetic spectrum for tissue treatment, are extensively used to treat a multitude of diverse skin conditions. Among other uses, non-invasive energy delivery devices may be used to tighten loose skin so that a patient appears younger, to remove skin spots or hair, or to kill bacteria.

One variety of these energy delivery devices emit high frequency electromagnetic energy in the radio-frequency (RF) band of the electromagnetic spectrum. The high frequency energy may be used to treat skin tissue non-ablatively and non-invasively by passing high frequency energy through a surface of the skin, while actively cooling the skin to prevent damage to the skin's epidermal layer closer to the skin surface. The high frequency energy heats tissue beneath the epidermis to a temperature sufficient to denature collagen, which causes the collagen to contract and shrink and, thereby, tighten the tissue. Treatment with high frequency energy also causes a mild inflammation. The inflammatory response of the tissue causes new collagen to be generated over time (between three days and six months following treatment), which results in further tissue contraction.

Typically, energy delivery devices include a treatment tip that is placed in contact with, or proximate to, the patient's skin surface and that emits electromagnetic energy that penetrates through the skin surface and into the tissue beneath the skin surface. The non-patient side of the energy delivery device, such as an electrode for high frequency energy, in the treatment tip may be sprayed with a coolant or cryogen spray under feedback control of temperature sensors for cooling tissue at shallow depths beneath the skin surface. A controller triggers the coolant spray based upon an evaluation of the temperature readings from temperature sensors in the treatment tip.

The cryogen spray may be used to pre-cool superficial tissue before delivering the electromagnetic energy. When the electromagnetic energy is delivered, the superficial tissue that has been cooled is protected from thermal effects. The target tissue that has not been cooled or that has received nominal cooling will warm up to therapeutic temperatures resulting in the desired therapeutic effect. The amount or duration of pre-cooling can be used to select the depth of the protected zone of untreated superficial tissue. After the delivery of electromagnetic energy has concluded, the cryogen spray may also be employed to prevent or reduce heat originating from treated tissue from conducting upward and heating the more superficial tissue that was cooled before treatment with the electromagnetic energy.

Although conventional methods apparatus and for delivering cryogen sprays have proved adequate for their intended purpose, what is needed are improved methods and apparatus for cooling superficial tissue in conjunction with non-ablative and non-invasive treatment of deeper regions of tissue beneath the skin surface with amounts of electromagnetic energy.

SUMMARY OF THE INVENTION

In one embodiment, a method is provided for treating tissue beneath a skin surface with electromagnetic energy. The method comprises pumping a fluid from a reservoir to an energy delivery device, circulating the fluid through the energy delivery device, and returning the fluid from the energy delivery device to the reservoir. The method further includes measuring a value of a room air temperature proximate to at least one of the energy delivery device or the reservoir, and adjusting a control temperature of the fluid in the reservoir based upon the measured value of the room air temperature. The electromagnetic energy is delivered from the energy delivery device to the tissue.

In another embodiment, an apparatus is provided for treating tissue beneath a skin surface with electromagnetic energy. The apparatus comprises an energy delivery device configured to deliver the electromagnetic energy to the tissue, a closed-loop cooling system including a reservoir configured to hold a coolant and a coldplate configured to regulate a temperature of the coolant held in the reservoir at a control temperature, and a temperature sensor configured to sense a room air temperature proximate to at least one of the reservoir or the energy delivery device. The closed-loop cooing system is configured to circulate the coolant between the energy delivery device and the reservoir. The apparatus further includes a temperature controller communicatively coupled to the coldplate, and a system controller communicatively coupled to the temperature sensor and to the temperature controller. The temperature controller is configured to operate the coldplate to maintain the coolant at the control temperature. The system controller is programmed to determine the control temperature based upon the room air temperature and communicate the control temperature to the temperature controller.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

FIG. 5 is an exploded view of the treatment tip of FIG. 2 in which the treatment electrode is shown in an unfolded condition.

FIG. 6 is a front perspective view of a manifold body located inside the treatment tip of FIG. 5.

FIG. 7 is a rear perspective view of the manifold body of FIG. 6.

DETAILED DESCRIPTION

Figure 1:
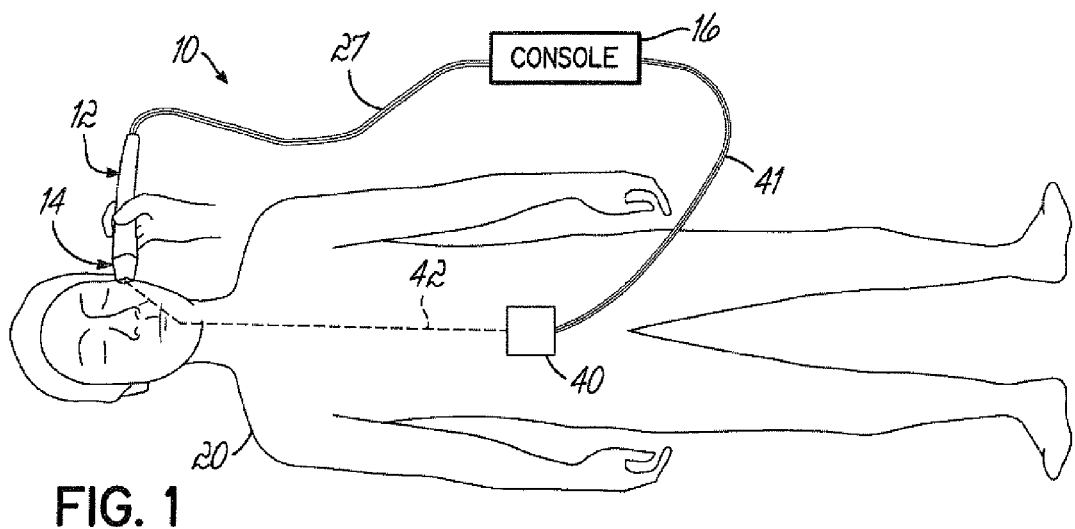
FIG. 1 is a diagrammatic view of a treatment system with a handpiece, a treatment tip, and a console in accordance with an embodiment of the invention

With reference to FIGS. 1-5, a treatment apparatus 10 includes a handpiece 12, a treatment tip 14 coupled in a removable and releasable manner with the handpiece 12, a console generally indicated by reference numeral 16, and a system controller 18. The system controller 18, which is incorporated into the console 16, controls the global operation of the different individual components of the treatment apparatus 10. Under the control of the system controller 18 and an operator's interaction with the system controller 18 at the console 16, the treatment apparatus 10 is adapted to selectively deliver electromagnetic energy in a high frequency band of the electromagnetic spectrum, such as the radiofrequency (RF) band to non-invasively heat a region of a patient's tissue to a targeted temperature range. The elevation in temperature may produce a desired treatment, such as removing or reducing wrinkles and otherwise tightening the skin to thereby improve the appearance of a patient 20 receiving the treatment. In alternative embodiments, the treatment apparatus 10 may be configured to deliver energy in the infrared band, microwave band, or another high frequency band of the electromagnetic spectrum, rather than energy in the RF band, to the patient's tissue.

The treatment tip 14 carries an energy delivery member in the representative form of a treatment electrode 22. The treatment electrode 22 is electrically coupled by conductors inside a cable 27 with a generator 38 configured to generate the electromagnetic energy used in the patient's treatment. In a representative embodiment, the treatment electrode 22 may have the form of a region 26 of an electrical conductor carried on an electrically-insulating substrate 28 composed of a dielectric material. In one embodiment, the substrate 28 may comprise a thin flexible base polymer film carrying the conductor region 26 and thin conductive (e.g., copper) traces or leads 24 on the substrate 28 that electrically couple the conductor region 26 with contact pads 25. The base polymer film may be, for example, polyimide or another material with a relatively high electrical resistivity and a relatively high thermal conductivity. The conductive leads 24 may contain copper or another material with a relatively high electrical conductivity. Instead of the representative solid conductor region 26, the conductor region 26 of treatment electrode 22 may include voids or holes unfilled by the conductor to provide a perforated appearance or, alternatively, may be segmented into plural individual electrodes that can be individually powered by the generator 38.

In one specific embodiment, the treatment electrode 22 may comprise a flex circuit in which the substrate 28 consists of a base polymer film and the conductor region 26 consists of a patterned conductive (i.e., copper) foil laminated to the base polymer film. In another specific embodiment, the treatment electrode 22 may comprise a flex circuit in which the conductor region 26 consists of patterned conductive (i.e., copper) metallization layers directly deposited the base polymer film by, for example, a vacuum deposition technique, such as sputter deposition. In each instance, the base polymer film constituting substrate 28 may be replaced by another non-conductive dielectric material and the conductive metallization layers or foil constituting the conductor region 26 may contain copper. Flex circuits, which are commonly used for flexible and high-density electronic interconnection applications, have a conventional construction understood by a person having ordinary skill in the art.

The substrate 28 includes a contact side 32 that is placed into contact with the skin surface of the patient 20 during treatment and a non-contact side 34 that is opposite to the contact side 32. The conductor region 26 of the treatment electrode 22 is physically carried on non-contact side 34 of the substrate 28. In the representative arrangement, the substrate 28 is interposed between the conductor region 26 and the treated tissue such that, during the non-invasive tissue treatment, electromagnetic energy is transmitted from the conductor region 26 through the thickness of the substrate 28 by capacitively coupling with the tissue of the patient 20.

When the treatment tip 14 is physically engaged with the handpiece 12, the contact pads 25 face toward the handpiece 12 and are electrically coupled with electrical contacts 36, such as pogo pin contacts, inside the handpiece 12. Electrical contacts 36 are electrically coupled with insulated and shielded conductors (not shown) of the electrical wiring 24 also located inside the handpiece 12. The insulated and shielded wires extend exteriorly of the handpiece 12 inside cable 27 to a generator 38 at the console 16. The generator 38, which has the form of a high frequency power supply, is equipped with an electrical circuit (not shown) operative to generate high frequency electrical current, typically in the radio-frequency (RF) region of the electromagnetic spectrum. The operating frequency of generator 38 may advantageously be in the range of several hundred kHz to about twenty (20) MHz to impart a therapeutic effect to treat target tissue beneath a patient's skin surface. The circuit in the generator 38 converts a line voltage into drive signals having an energy content and duty cycle appropriate for the amount of power and the mode of operation that have been selected by the clinician, as understood by a person having ordinary skill in the art. In one embodiment, the generator 38 is a 400-watt, 6.78 MHz high frequency generator.

A non-therapeutic passive or return electrode 40, which is electrically coupled with the generator 38, is physically attached to a site on the body surface of the patient 20, such as the patient's lower back. During treatment, high frequency current flows from the treatment electrode 22 through the treated tissue and the intervening bulk of the patient 20 to the return electrode 40 and then through conductors inside a return cable 41 to define a closed circuit or current path 42. Because of the relatively large surface area of the return electrode 40 in contact with the patient 20, the current density flowing from the patient 20 to the return electrode 40 is relatively low in comparison with the current density flowing from the treatment electrode 22 to the patient 20. As a result, the return electrode 40 is non-therapeutic because negligible heating is produced at its attachment site to the patient 20. High frequency electrical current flowing between the treatment electrode 22 and the patient 20 is maximized at the skin surface and underlying tissue region adjacent to the treatment electrode 22 and, therefore, delivers a therapeutic effect to the tissue region near the treatment site.

Figure 3:
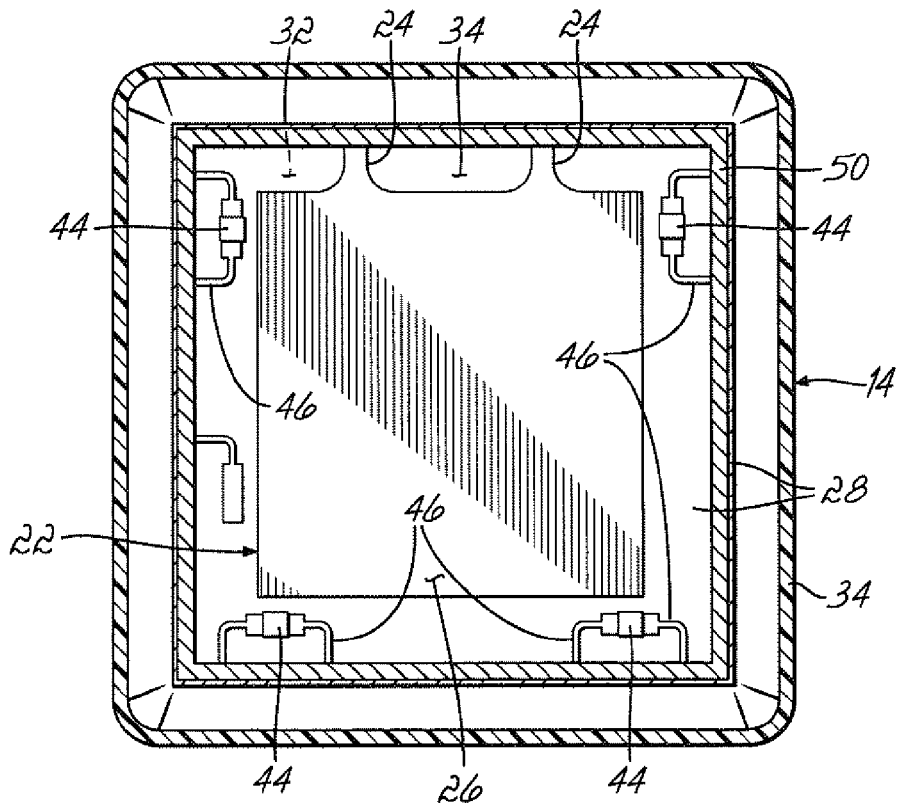
FIG. 3 is a rear view of the assembled treatment tip taken generally along line 3-3 in FIG. 2 showing the electrode and temperature sensors.

As best shown in FIG. 3, the treatment tip 14 includes temperature sensors 44, such as thermistors or thermocouples, that are located on the non-contact side 34 of the substrate 28 that is not in contact with the patient's skin surface. Typically, the temperature sensors 44 are arranged about the perimeter of the conductor region 26 of the treatment electrode 22. Temperature sensors 44 are constructed to detect the temperature of the treatment electrode 22 and/or treatment tip 14, which may be representative of the temperature of the treated tissue. Each of the temperature sensors 44 is electrically coupled by conductive leads 46 with one or more of the contact pads 25, which are used to supply direct current (DC) voltages from the system controller 18 through the electrical wiring 26 to the temperature sensors 44.

With continued reference to FIGS. 1-5, the system controller 18 regulates the power delivered from the generator 38 to the treatment electrode 22 and otherwise controls and supervises the operational parameters of the treatment apparatus 10. The system controller 18 may include user input devices to, for example, adjust the applied voltage level of generator 38. The system controller 18 includes a processor, which may be any suitable conventional microprocessor, microcontroller or digital signal processor, executing software to implement control algorithms for the operation of the generator 38. System controller 18, which may also include a nonvolatile memory (not shown) containing programmed instructions for the processor, may be optionally integrated into the generator 38. System controller 18 may also communicate, for example, with a nonvolatile memory carried by the handpiece 12 or by the treatment tip 14. The system controller 18 also includes circuitry for supplying the DC voltages and circuitry that relates changes in the DC voltages to the temperature detected by the temperature sensors 44, as well as temperature sensors 90 and 88.

Figure 4:
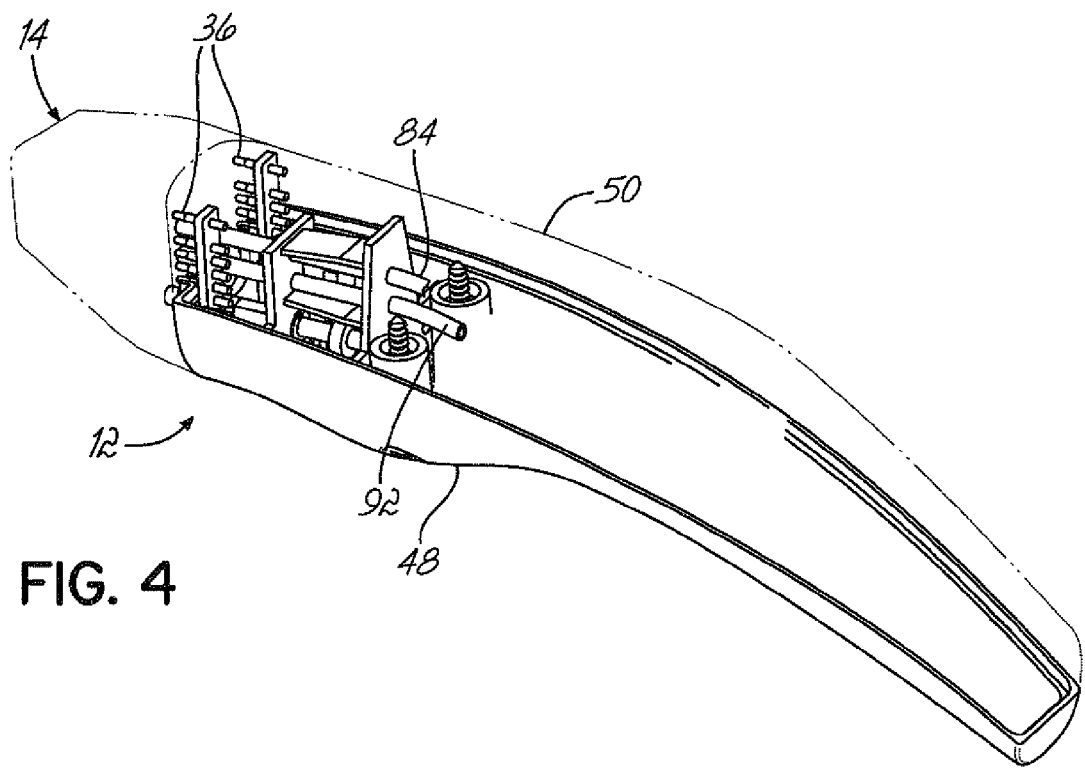
FIG. 4 is a perspective view of the handpiece partially shown in phantom in which certain internal components, such as electrical wiring, are omitted for clarity.

With specific reference to FIG. 4, the handpiece 12 is constructed from a body 48 and a cover 50 that is assembled with conventional fasteners with the body 48. The assembled handpiece 12 has a smoothly contoured shape suitable for manipulation by a clinician to maneuver the treatment tip 14 and treatment electrode 22 to a location proximate to the skin surface and, typically, in a contacting relationship with the skin surface. An activation button (not shown), which is accessible to the clinician from the exterior of the handpiece 12, is depressed for closing a switch that energizes the treatment electrode 22 and, thereby, delivers high frequency energy over a short delivery cycle to treat the target tissue. Releasing the activation button opens the switch to discontinue the delivery of high frequency energy to the patient's skin surface and underlying tissue. After the treatment of one site is concluded, the handpiece 12 is manipulated to position the treatment tip 14 near a different site on the skin surface for another delivery cycle of high frequency energy delivery to the patient's tissue.

With reference to FIGS. 5-7, the treatment tip 14 includes a rigid outer shell 52, a rear cover 54 that is coupled with an open rearward end of the outer shell 52, a manifold body 55 disposed inside an enclosure or housing inside the outer shell 52, and a flange 53 for the rear cover 54. The flange 53 may be a portion of the manifold body 55. A portion of the substrate 28 overlying the conductor region 26 of the treatment electrode 22 is exposed through a window 56 defined in a forward open end of the outer shell 52. The substrate 28 is wrapped or folded about the manifold body 55. The flange 53 provides a flat support surface over which the contact pads 25 are placed, such that the electrical contacts 36 press firmly against the contact pads 25.

As best shown in FIGS. 5 and 6, the manifold body 55, which may be formed from an injection molded polymer resin, includes a front section 60, a stem 62 projecting rearwardly from the front section 60, and ribs 64 on the stem 62 used to position the manifold body 55 inside the outer shell 52. The front section 60 of the manifold body 55 includes a channel 66 that, in the assembly constituting treatment tip 14, underlines the conductor region 26 of the treatment electrode 22. The shape of the front section 60 corresponds with the shape of the window 56 in the outer shell 52. The substrate 28 of the treatment electrode 22 is bonded with a rim 68 of the manifold body 55 to provide a fluid seal that confines coolant flowing in the channel 66. The area inside the rim 68 is approximately equal to the area of the conductor region 26 of treatment electrode 22. Channel 66 includes convolutions that are configured to optimize the residence time of the coolant in channel 66, which may in turn optimize the heat transfer between the coolant and the treatment electrode 22.

As best shown in FIGS. 5-7, an inlet bore or passage 70 and an outlet bore or passage 72 extend through the stem 62 of the manifold body 55. The inlet passage 70 and outlet passage 72 are rearwardly accessible through an oval-shaped slot 74 defined in the rear cover 54. The inlet passage 70 intersects the channel 66 at an inlet 76 to the channel 66 and the outlet passage 72 intersects the channel 66 at an outlet 78 from the channel 66. The channel 66 is split into two channel sections 80, 82 so that fluid flow in the channel 66 diverges away in two separate streams from the inlet 76 and converges together to flow into the outlet 78. Fluid pressure causes the coolant to flow from the inlet 76 through the two channel sections 80, 82 to the outlet 78 and into the outlet passage 72.

With reference to FIGS. 2 and 5-7, fluid connections are established with the inlet passage 70 and the outlet passage 72 to establish the closed circulation loop and permit coolant flow to the channel 66 in the manifold body 55 when the treatment tip 14 is mated with the handpiece 12. Specifically, the outlet passage 72 is coupled with a return line 84 in the form of a fluid conduit or tube. The inlet passage 70 is coupled with a supply line 86 in the form of an inlet conduit or tube. The return line 84 and the supply lines 86 extend out of the handpiece 12 and are routed to the console 16. The inlet passage 70 and the outlet passage 72 may include fittings (not shown) that facilitate the establishment of fluid-tight connections.

Figure 2:
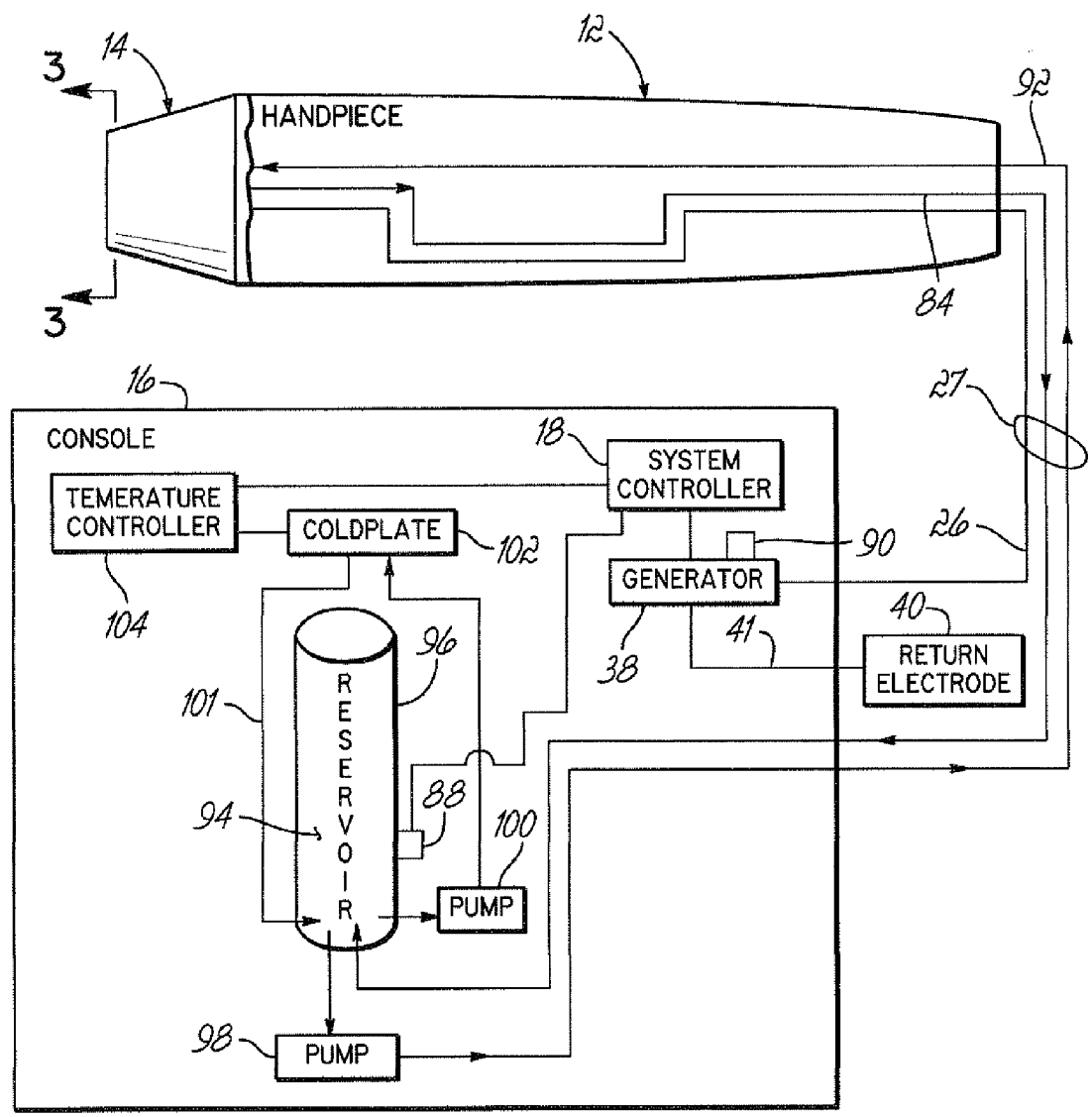
FIG. 2 is a diagrammatic view of the handpiece, treatment tip, and console of FIG. 1 showing a closed-loop cooling system of the treatment system.

With reference to FIG. 2, the treatment apparatus 10 is equipped with a closed loop cooling system that includes the manifold body 55 located inside the treatment tip 14. The closed loop cooling system further includes a reservoir 96 holding a volume of a coolant 94 and a pump 98, which may be a diaphragm pump, that continuously pumps a stream of the coolant from an outlet of the reservoir 96 through the supply line 86 to the manifold body 55 in the treatment tip 14. The manifold body 55 is coupled in fluid communication with the reservoir 96 by the return line 84. The return line 84 conveys the coolant 94 from the treatment tip 14 back to the reservoir 96 to complete the circulation loop.

Heat generated in the treatment tip 14 by energy delivery from the treatment electrode 22 and heat transferred from the patient's skin and an underlying depth of heated tissue is conducted through the substrate 28 and treatment electrode 22. The heat is absorbed by the circulating coolant 94 in the channel 66 of the manifold body 55, which lowers the temperature of the treatment electrode 22 and substrate 28 and, thereby, cools the patient's skin and the underlying depth of heated tissue. The contact cooling, at the least, assists in regulating the depth over which the tissue is heated to a therapeutic temperature by the delivered electromagnetic energy.

The coolant 94 stored in the reservoir 96 is chilled by a separate circulation loop 101 that pumps coolant 94 from the reservoir 96 through separate supply and return lines to a coldplate 102. A pump 100, which may be a centrifugal pump, pumps the coolant 94 under pressure from the reservoir 96 to the coldplate 102. In an alternative embodiment, the coldplate 102 may be placed directly in the return line 84 if permitted by the capacity of the coldplate 102 and system flow constrictions.

In a representative embodiment, the coldplate 102 may be a liquid-to-air heat exchanger that includes a liquid heat sink with a channel (not shown) for circulating the coolant 94, a thermoelectric module (not shown), and an air-cooled heat sink (not shown). A cold side of the thermoelectric module in coldplate 102 is thermally coupled with the liquid heat sink and a hot side of the thermoelectric module in coldplate 102 is thermally coupled with the air-cooled heat sink. The cold side is cooled for extracting heat from the coolant 94 flowing through the liquid heat sink. As understood by a person having ordinary skill in the art, an array of semiconductor couples in the thermoelectric module operate, when biased, by the Peltier effect to convert electrical energy into heat pumping energy. Heat flows from the liquid heat sink through the thermoelectric elements to the air-cooled heat sink. The air-cooled heat sink of the liquid-to-air heat exchanger dissipates the heat extracted from the coolant 94 circulating in the liquid heat sink to the surrounding environment. The air-cooled heat sink may be any conventional structure, such as a fin stack with a fan promoting convective cooling.

A temperature controller 104 inside the console 16 is electrically coupled with the coldplate 102 and is also electrically coupled with the system controller 18. The system controller 18, which is electrically coupled with a temperature sensor 88 used to measure the coolant temperature in the reservoir 96, supplies temperature control signals to the temperature controller 104 in response to the measured coolant temperature. Under the feedback control, the temperature controller 104 reacts to the control temperature communicated from the temperature controller to control the operation of the coldplate 102 and, thereby, regulate the temperature of the coolant 94 in the reservoir 96.

Because the coolant 94 is at a temperature below room air temperature, the coolant 94 inevitably warms as it flows through supply line 86 from the console 16 through the ambient environment to the handpiece 12. As a result, the coolant temperature at the manifold body 55 is higher than the coolant temperature at the reservoir 96. Although the warming can be minimized by insulating the exterior of the supply line 86 to limit heat gain from the environment, the heat gain cannot be eliminated. Further complicating the problem, the amount of heat transferred to the coolant 94 will vary based on the room air temperature and fluid flow rate. Typically, the coolant temperature in the manifold body 55 determines the temperature gradient with depth into the patient's tissue, which may impact the depth profile of the tissue treatment.

To compensate for the heat gain, the coolant 94 in the reservoir 96 is maintained at a lower temperature than required at the treatment tip 14. Generally, the amount of the over-cooling compensation for the coolant 94 in the reservoir 96 will scale upwardly with as the room air temperature increases. Coolant 94 originating from the reservoir 96 with a given initial temperature will experience a greater heat gain if the apparatus 10 is located in a comparatively warmer room. In other words, the heat gained by the coolant 94 flowing in the supply line 92 increases with increasing difference between the coolant temperature and the room air temperature.

The heat gain can be compensated by adjusting the coolant temperature at the reservoir 96. The value of the coolant temperature inside the reservoir 96 may be set based upon the temperature of the room air in which the treatment apparatus 10 is immersed. To that end, the room air temperature may be detected by a temperature sensor 90, such as a thermocouple, or a thermistor located at the console 16. In one embodiment, the temperature sensor 90 may be associated with the generator 38. Alternatively, the temperature sensor 90 may be located at other locations proximate to the components of the treatment apparatus 10, such as attached to the handpiece 12.

The room air temperature measured by the temperature sensor 90 is communicated to the system controller 18 and may be used by the system controller 18 for other purposes, such as controlling cooling fans used to dissipate heat generated inside the console 16.

A reference is established to guide the selection of coolant temperature at the reservoir 96. Specifically, empirical data may be accumulated to assess the heat gain of the coolant 94, while flowing in the supply line 92 from the console 16 to the manifold body 55, as a function of room air temperature. In one embodiment, the temperature sensors 44 in the treatment tip 14 may be used to sense the coolant temperature at the manifold body 55 and a temperature sensor 88 may be used to sense the coolant temperature in the reservoir 96. These temperatures are communicated to the system controller 18, which determines a temperature change at each value of the room air temperature at which the empirical data is acquired. For example, the temperatures of the coolant 94 at the manifold body 55 and at the reservoir 96 can be measured and the temperature change assessed as the room air temperature is varied from over a range, such as from 60° F. to 85° F.

The empirical data may be acquired at a single reservoir coolant temperature if temperature change due to heat gain is relatively insensitive to reservoir coolant temperature over the normal range of values used during treatment. Otherwise, the empirical date is acquired at a series of reservoir coolant temperatures. The empirical data may be acquired at a single flow rate if temperature change is relatively insensitive to flow rate over the normal range of values used during treatment. Otherwise, the empirical date is acquired at a series of flow rates for the coolant 94, as pumped by pump 98, in the supply line 92.

Armed with knowledge of the temperature change due to heat gain by the coolant flowing in the supply line 92 as a function of room air temperature, a control technique for measuring the room air temperature and adjusting the coolant temperature at the reservoir 96 based upon the measured room air temperature is implemented in the system controller 18. The temperature change is used to adjust the degree of undercooling of the coolant 94 in the reservoir 96, which effectively makes the coolant temperature at the treatment tip 14 independent of air temperature or, at the least, reduces the dependence of the coolant temperature at the treatment tip 14 on air temperature. Several approaches are available for determining the targeted temperature for the coolant 94 in the reservoir 96 during system operation that compensates for the heat gain experienced by the coolant 94 while flowing in the supply line 92.

In one embodiment, the data relating the temperature change as a function of room air temperature is stored as entries in a lookup table and the system controller 18 may include logic that controls the lookup table in the address space of the controller's random access memory. The lookup table represents a data structure, usually an array or an associative array, that contains multiple entries. Within each individual entry in the database, a temperature change is specified for a given room air temperature, as well as potentially other variables like coolant flow rate. In the latter instance, the data structure of the lookup table is a two-dimensional array or associative array that associates a temperature change with each measured room air temperature. The lookup table, which may be also be stored in a non-volatile memory of the system controller 18, may be used to replace a runtime computation with a simpler lookup operation that merely requires the software executing on the system controller 18 to access numerical values stored in memory.

The control temperature for the coolant 94 stored in the reservoir 96 may be established with the assistance of the lookup table. As required, the system controller 18 accesses the lookup table to retrieve a value of temperature change from memory that is correlated in the data structure with the corresponding room air temperature. If the measured room air temperature fails to coincide exactly with one of the values in the lookup table, a temperature change can be interpolated from the numerical values in the table. The system controller 18 may specify an adjustment as an offset to the reservoir coolant temperature when a treatment is initiated and maintain that reservoir coolant temperature at that adjusted reservoir coolant temperature over the duration of the patient treatment. The system controller 18 implements the mathematical relationship in software executing on its processor to determine a control temperature that is communicated to the temperature controller 104 for use in regulating the operation of the coldplate 102 to establish and maintain the coolant in the reservoir 96 at the control temperature.

In an alternative version of the look-up table embodiment, the system controller 18 may monitor the room air temperature for deviations of significance and perform real-time adjustments during the course of patient treatment. If a significant deviation is detected, the system controller 18 may retrieve a different numerical value of temperature change from the lookup table and implement a revised reservoir coolant temperature by supplying an updated control temperature to the temperature controller 104 for use in adjusting the operation of the coldplate 102.

In another embodiment of the invention, the correlation between the measured ambient temperature and the temperature change for use in over-cooling the coolant 94 in the reservoir 96 may be determined by a run-time computation using a mathematical equation or relationship. The mathematical relationship is established from the empirically measured data array associating temperature change as a function of room air temperature. For example, the empirically measured data array may be statistically analyzed by a linear regression to establish a mathematical relationship that is linear such that the temperature change that is used to adjust the reservoir coolant temperature scales linearly with the room air temperature. The system controller 18 implements the mathematical relationship in software executing on its processor to determine a control temperature that is communicated to the temperature controller 104 for use in regulating the operation of the coldplate 102 to establish and maintain the coolant in the reservoir 96 at the control temperature.

In an alternative version of the equation-based embodiment, the system controller 18 may monitor the room air temperature communicated from the temperature sensor 90 to detect deviations of significance and perform real-time adjustments during the course of patient treatment. If a significant deviation is detected, the system controller 18 may recalculate a different numerical value of temperature change using the mathematical relationship and implement a revised reservoir coolant temperature by supplying an updated control temperature to the temperature controller 104 for use in adjusting the operation of the coldplate 102.

In use and with reference to FIGS. 1-7, the coolant 94 is circulated by pump 100 between the coldplate 102 and the reservoir 96. The system controller 18 monitors the temperature of the coolant 94 in the reservoir 96 using temperature information received from temperature sensor 88 and communicates control signals to the temperature controller 104 to establish a control temperature for the coolant 94 in the reservoir 96. The system controller 18 samples the room air temperature communicated from the temperature sensor 90 and adjusts the coolant temperature in the reservoir 96 to reflect the room air temperature measured with the aid of temperature sensor 90. Specifically, the system controller 18 communicates the control temperature to the temperature controller 104, which adjusting the operation of the coldplate 102 to establish the coolant temperature in the reservoir 96.

The coolant temperature is established by the temperature controller 104 in the reservoir 96 at a calculated temperature setting that is less than the minimum desired temperature at the treatment tip 14. In other words, the coolant temperature in the reservoir 96 is set at a value that is colder than the coolant temperature required at the treatment tip 14. The specific temperature is set based upon the room air temperature measured by temperature sensor 90. As described above, an offset to the reservoir coolant temperature is either retrieved by the system controller 18 from a lookup table or calculated by the system controller 18 using a mathematical relationship. The calculated or retrieved offset is used by the system controller 18 to adjust the control temperature for the coolant 94 in the reservoir 96. By cooling the coolant 94 to a temperature less than desired based upon the measured room air temperature, coolant 94 can be delivered to the treatment tip 14 at the desired temperature at much greater accuracy than without this process.

The treatment electrode 22 is energized by generator 38 to deliver doses of high frequency energy to the target tissue. During patient treatment, coolant 94 is continuously pumped by pump 98 through the supply line 86 from the reservoir 96 to the handpiece 12. The coolant 94 is delivered to the manifold body 55 and circulated through the channel 66 in contact with the conductor region 26 of treatment electrode 22 on the non-contact side 34 of substrate 28. This cools the treatment electrode 22, which in turn cools the tissue immediately beneath the patient's skin surface in the contacting relationship with the contact side 32 of the substrate 28. Spent coolant 94 is directed from the channel 66 into the return line 84 and returned to the reservoir 96.

The continuous stream of coolant 94 flowing through the channel 66 in the manifold body 55 continuously cools the adjacent tissue contacted by the treatment electrode 22. The contact cooling prevents superficial tissue from being heated to a temperature sufficient to cause a significant and possibly damaging thermal effect. Depths of tissue that are not significantly cooled by thermal energy transfer to the continuous stream of coolant 94 flowing through the channel 66 in manifold body 55 will be warmed by the high frequency energy to therapeutic temperatures resulting in the desired therapeutic effect. The amount or duration of pre-cooling, after the treatment electrode 22 is contacted with the skin surface and before electromagnetic energy is delivered, may be used to select the protected depth of untreated tissue. Longer durations of pre-cooling and lower coolant temperatures produce a deeper protected zone and, hence, a deeper level in tissue for the onset of the treatment zone.

Using the same mechanism, the tissue is also cooled by the continuous stream of coolant 94 flowing through the manifold body 55 during energy delivery and after heating by the transferred high frequency energy. Post-cooling may prevent or reduce heat delivered deeper into the tissue from conducting upward and heating shallower depths to therapeutic temperatures even though external energy delivery from the treatment electrode 22 to the targeted tissue has ceased.

If the system controller 18 detects a significant deviation in room air temperature during treatment, the system controller 18 may optionally determine and communicate an updated control temperature to the temperature controller 104.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method for treating tissue beneath a skin surface with electromagnetic energy, the method comprising:
   pumping a fluid from a reservoir to an energy delivery device;
   circulating the fluid through the energy delivery device;
   returning the fluid from the energy delivery device to the reservoir;
   measuring a value of a room air temperature proximate to at least one of the energy delivery device or the reservoir;
   adjusting a control temperature of the fluid in the reservoir based upon the measured value of the room air temperature; and
   delivering the electromagnetic energy from the energy delivery device to the tissue.

2. The method of claim 1 wherein adjusting the control temperature of the fluid in the reservoir further comprises:
   based upon the value of the room air temperature and a desired fluid temperature at the energy delivery device, retrieving a numerical adjustment to the control temperature from a lookup table stored in a memory.

3. The method of claim 2 further comprising:
   storing the numerical adjustment as an entry in the lookup table in the memory.

4. The method of claim 2 wherein the lookup table contains a data array correlating a change in the control temperature between the reservoir and the energy delivery device with the room air temperature, and further comprising:
   storing the data array of the lookup table in the memory.

5. The method of claim 4 wherein the memory is included in a system controller configured to control operation of the energy delivery device, and further comprising:
   measuring the change in the control temperature and a desired fluid temperature at the energy delivery device as a function of the room air temperature; and
   generating the lookup table with the system controller from the measured change at each room air temperature.

6. The method of claim 1 wherein operation of the energy delivery device is controlled by a system controller, and adjusting the control temperature of the fluid in the reservoir further comprises:
   calculating with the system controller a numerical adjustment to the control temperature using a mathematical relationship relating the control temperature to the room air temperature.

7. The method of claim 6 further comprising:
   measuring a change in the control temperature as a function of the room air temperature; and
   generating with the system controller the mathematical relationship from the measured change in the control temperature at each different room air temperature.

8. The method of claim 1 further comprising:
   re-measuring the value of the room air temperature proximate to at least one of the energy delivery device or the reservoir; and
   adjusting the control temperature of the fluid in the reservoir based upon the re-measured value of the room air temperature.

9. The method of claim 1 wherein adjusting the control temperature of the fluid in the reservoir further comprises:
   cooling the fluid in the reservoir such that the control temperature is below the desired temperature at the energy delivery device.

10. The method of claim 9 wherein adjusting the control temperature of the fluid in the reservoir further comprises:
    determining an adjustment to the control temperature based upon the value of the room air temperature;
    communicating the adjustment to a temperature controller for a coldplate; and
    circulating the fluid from the reservoir to the coldplate configured to cool the fluid sufficiently to maintain the fluid in the reservoir at the adjusted control temperature.

11. The method of claim 1 wherein the electromagnetic energy heats the tissue, and further comprising:
    contacting the skin surface with a portion of the energy delivery device while delivering the electromagnetic energy to heat the tissue; and
    cooling a region of the heated tissue beneath the contacted skin surface with the fluid circulating through the energy delivery device.

12. The method of claim 1 wherein the electromagnetic energy heats the tissue, and further comprising:
    contacting the skin surface with a portion of the energy delivery device while delivering the electromagnetic energy to heat the tissue in a non-invasive manner; and
    cooling a region of the heated tissue beneath the contacted skin surface with the fluid circulating through the energy delivery device.

13. The method of claim 1 wherein the electromagnetic energy is delivered to the tissue by capacitively coupling and heat the tissue, and further comprising:
    cooling a region of the heated tissue beneath the skin surface with the fluid circulating through the energy delivery device.

* * * * *

UNITED STATES PATENT AND TRADEMARK OFFICE
CERTIFICATE OF CORRECTION

| | | |
|---|---|---|
| PATENT NO. | : 8,515,553 B2 | Page 1 of 1 |
| APPLICATION NO. | : 12/110384 | |
| DATED | : August 20, 2013 | |
| INVENTOR(S) | : Alan Schenck | |

It is certified that error appears in the above-identified patent and that said Letters Patent is hereby corrected as shown below:

In the Specification:

At column 2, line number 1, change "apparatus and" to --and apparatus-- and at line 32, change "cooing" to --cooling--.

Column 3, line 60, after "deposited" insert --on--.

Column 7, line 49, after "upwardly" delete "with".

Column 8, line 63, after "may" delete "be".

Column 10, line 5, change "adjusting" to --adjusts--.

In the Claims:

At column 12, claim number 13, line number 49, change "heat" to --heating--.

Signed and Sealed this
Twelfth Day of November, 2013

Teresa Stanek Rea
*Deputy Director of the United States Patent and Trademark Office*